United States Patent
Olt et al.

(10) Patent No.: US 9,091,674 B2
(45) Date of Patent: Jul. 28, 2015

(54) MEANS AND METHOD FOR DETERMINING CHEMICAL OXYGEN DEMAND

(71) Applicant: MERCK PATENT GMBH, Darmstadt (DE)

(72) Inventors: Ralf Olt, Luetzelbach-Seckmauern (DE); Gunter Decker, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/364,158

(22) PCT Filed: Nov. 16, 2012

(86) PCT No.: PCT/EP2012/004761
§ 371 (c)(1),
(2) Date: Jun. 10, 2014

(87) PCT Pub. No.: WO2013/087143
PCT Pub. Date: Jun. 20, 2013

(65) Prior Publication Data
US 2014/0322814 A1    Oct. 30, 2014

(30) Foreign Application Priority Data
Dec. 12, 2011    (EP) .................................... 11009778

(51) Int. Cl.
*G01N 33/18*    (2006.01)
*G01N 21/31*    (2006.01)

(52) U.S. Cl.
CPC .......... *G01N 33/1806* (2013.01); *G01N 21/314* (2013.01)

(58) Field of Classification Search
CPC ..... G01N 21/31; G01N 21/314; G01N 33/18; G01N 33/1806; Y10T 436/15; Y10T 436/156666; Y10T 436/18; Y10T 436/25; Y10T 436/25125
USPC .......... 436/62, 79, 80, 81, 83, 100, 102, 119, 436/147, 164, 166, 174, 175; 422/79, 422/82.05, 82.09
See application file for complete search history.

(56) References Cited

U.S. PATENT DOCUMENTS

| | | | | |
|---|---|---|---|---|
| 3,540,845 | A | * | 11/1970 | Hickey et al. ................... 436/62 |
| 3,674,370 | A | | 7/1972 | Jonsson et al. |
| 3,930,798 | A | * | 1/1976 | Schierjott et al. ............... 436/62 |
| 5,496,739 | A | * | 3/1996 | Loescher et al. .............. 436/131 |
| 2011/0027893 | A1 | | 2/2011 | Kathe et al. |

FOREIGN PATENT DOCUMENTS

| | | |
|---|---|---|
| CN | 2720437 Y | 8/2005 |
| CN | 101450829 A | 6/2009 |
| DE | 2022640 A1 | 11/1970 |

OTHER PUBLICATIONS

International Search Report for PCT/EP2012/004761 dated Mar. 18, 2013.
English Abstract of CN2720437, Publication Date: Aug. 24, 2005.
English Abstract of CN101450829, Publication Date: Jun. 10, 2009.

* cited by examiner

*Primary Examiner* — Maureen Wallenhorst
(74) *Attorney, Agent, or Firm* — Millen, White, Zelano & Branigan, P.C.

(57) ABSTRACT

The invention relates to a means and a method for the photometric determination of the chemical oxygen demand of chloride-containing samples.

9 Claims, No Drawings

MEANS AND METHOD FOR DETERMINING CHEMICAL OXYGEN DEMAND

The invention relates to a means and a method for the photometric determination of the chemical oxygen demand of chloride-containing samples.

The chemical oxygen demand (COD) is, as sum parameter, a measure of the sum of all substances present in water which can be oxidised under certain conditions. It indicates the amount of oxygen (in mg/l) which would be required for their oxidation if oxygen were the oxidant. The method is also, under the name "Cr-VI oxidisability" (chromate consumption if this were the oxidant), compared with the potassium permanganate consumption ("Mn-VII oxidisability"). Besides this use as a measure of the concentration of chemically oxidisable substances in water, the chemical oxygen demand is also used as a measure of the chemically oxidisable substances which are released into the waste water in the case of the production of an amount of product (g/kg of product) or which are disposed of in a time period (t/a, tonnes per year).

In order to determine the COD, a water sample is strongly acidified using sulfuric acid and heated with a prespecified precise amount of the strong oxidant potassium dichromate ($K_2Cr_2O_7$) with addition of silver sulfate as catalyst.

DIN 38409-41 (also DEV H41) describes the determination of the COD by means of titration. This standard describes, under method 41-1, a titrimetric method for samples having a chloride content up to 1000 mg/l.

Under method 41-2, a method is described for the reduction in the chloride content of samples having a chloride content above 1000 mg/l. After the reduction in the content, the COD can be determined by means of titration as described under 41-1.

In particular for monitoring the COD in sewage treatment plants and other water-treatment facilities in which a laboratory and trained laboratory personnel is not available, however, the COD determination is usually carried out by means of so-called cell tests (rapid methods). These test kits can also be used in the case of little prior knowledge, already contain all necessary reagents and require only little laboratory equipment. In this method, the dichromate consumption is not determined titrimetrically, but instead photometrically.

DIN ISO 15705 describes the photometric determination of the COD by means of the cell test. However, this determination is restricted to samples having a chloride content of max. 1000 mg/l.

COD cell tests are available from various suppliers which, through variation of the sample/reagent ratio and an increase in the mercury (II) sulfate amount in the reagents, enable determination of samples having a chloride content up to 5000 mg/l at the same time as a COD content of up to 2000 mg/l.

Pre-dilution of the samples with dist. water and dilution of the samples with reagents also enable a higher chloride tolerance to be achieved, but the COD content of the sample is also diluted at the same time. This procedure is therefore not suitable for samples having a low COD content.

A sample having a COD content of below 2000 mg/l and a chloride content above 5000 mg/l cannot to date be analysed by means of a cell test. Only the significantly more complex titration method is available for this purpose. The reason for this restriction is that samples having a chloride content of above 5000 mg/l must firstly be reduced in content in accordance with DIN 38409-41, method 41-2. According to the standard, 25 ml of concentrated sulfuric acid are for this purpose added to 20 ml of the analysis sample, and the mixture is stirred for a number of hours. The chloride is thus expelled as hydrogen chloride. The sulfuric acid sample thereby obtained is not suitable for determination of the COD by means of the cell test in accordance with DIN ISO 15705.

However, this represents a severe restriction of the applicability of the cell test, since, for example, chloride-containing industrial waste water or sea water samples cannot to date be investigated by means of a cell test in accordance with DIN ISO 15705.

The object of the present invention was therefore to provide a cell test, preferably using simple, ready-to-use reagents, which is also suitable for starting samples having a COD content of below 2000 mg/l and a chloride content above 5000 mg/l. After reduction of the chloride content for the COD determination, these samples have a high sulfuric acid content.

It has now been found that a certain composition of the reagent solution for the cell test makes this also suitable for determination of the COD in samples in which the chloride content has been reduced. In addition, it has been found that the reagent solution according to the invention enables for the first time the photometric determination of the COD content of, for example, samples in which the chloride content has been reduced in accordance with DIN 38409-41-2 by means of a reagent solution which does not contain any toxic mercury (II) sulfate.

The present invention therefore relates to a cell containing a reagent solution at least consisting of
  potassium dichromate ($K_2Cr_2O_7$)
  silver sulfate ($Ag_2SO_4$)
  water
  sulfuric acid
characterised in that the sulfuric acid content is between 20 and 50% (w/w).

In a preferred embodiment, the cell can be sealed reversibly.

In an embodiment, the reagent solution additionally contains mercury (II) sulfate ($HgSO_4$).

In a preferred embodiment, the reagent solution consists only of 0.1 to 2.5% by weight of potassium dichromate ($K_2Cr_2O_7$), 0.1 to 2% by weight of silver sulfate ($Ag_2SO_4$), 20 to 50% by weight of sulfuric acid and water.

In a preferred embodiment, the reagent solution is prepared by mixing at least one solution which contains at least potassium dichromate and water, but no silver sulfate and no mercury(II) sulfate, and a solution which contains at least silver sulfate and sulfuric acid, but no mercury sulfate and no potassium dichromate.

The present invention also relates to a method for the determination of the COD content in chloride-containing samples by
  a) expulsion of the chloride ions from the sample by treatment of the sample with sulfuric acid
  b) mixing of at least some of the sample obtained from step a) with a reagent solution at least consisting of
    potassium dichromate ($K_2Cr_2O_7$)
    silver sulfate ($Ag_2SO_4$)
    optionally mercury (II) sulfate ($HgSO_4$)
    water
    sulfuric acid
  where the sulfuric acid content is between 20 and 50% (w/w)
  c) incubation of the mixture from step b) for at least 20 minutes at a temperature above 100° C.
  d) photometric determination of the COD content of the mixture from c)

In a preferred embodiment, method steps b) to d) are carried out in a cell which can be sealed reversibly.

In a preferred embodiment, the expulsion in step a) is carried out using concentrated sulfuric acid.

In a preferred embodiment, the incubation in step c) is carried out for 20 to 150 minutes at a temperature between 140 and 180° C.

In a preferred embodiment, the sample and the reagent solution are mixed in step b) in a sample : reagent solution volume ratio between 5:1 and 2:1.

In a preferred embodiment, the reagent solution consists only of 0.1 to 2.5% by weight of potassium dichromate ($K_2Cr_2O_7$), 0.1 to 2% by weight of silver sulfate ($Ag_2SO_4$), 20 to 50% by weight of sulfuric acid and water.

In a preferred embodiment, the reagent solution is prepared by mixing at least one solution which contains at least potassium dichromate and water, but no silver sulfate and no mercury (II) sulfate, and a solution which contains at least silver sulfate and sulfuric acid, but no mercury sulfate and no potassium dichromate.

In a preferred embodiment, the photometric determination in step c) is carried out by measurement of the absorbance at a wavelength in the range from 300-700 nm.

In a further preferred embodiment, sulfuric acid having a COD content of less than 5 mg/l is employed for the preparation of the reagent solution.

In a further preferred embodiment, sulfuric acid having a COD content of less than 5 mg/l is employed for the reduction in the chloride content, preferably carried out in accordance with DIN 38409-41-2.

In accordance with the invention, a cell is a vessel in which photometric measurements can be carried out. Cells typically consist of quartz, glass or plastic and have at least two plane-parallel side surfaces or are round. Preference is given to round cells. In addition, preference is given in accordance with the invention to cells which can be sealed reversibly. These cells which can be sealed reversibly and preferably in a gas-tight manner can be used directly as vessel for carrying out the method according to the invention. To this end, the cells can already be filled with the reagent solution and stored. The sample can then be added, and the cell can be resealed tightly for the incubation and the subsequent method steps.

In order to determine the COD reliably and comparably, extremely constant reaction determinations must be present. These reaction conditions are specified, for example, by the DIN standards DIN 38409-41 and DIN ISO 15705. The performance of a COD determination is generally known to the person skilled in the art. Details are given in the DIN standards.

The method according to the invention is also suitable, if constant reaction conditions are maintained, for the determination of the COD with a sensitivity and constancy comparable to the DIN standards.

While samples having a chloride content above 5000 mg/l could hitherto only be measured reliably titrimetrically, this can in accordance with the invention now also be carried out photometrically. It has been found that a reduction in the sulfuric acid content in the reagent solution also makes samples having a high sulfuric acid content suitable for photometric measurement. To date, it was regarded as difficult reliably to prepare reagent solutions having a lower sulfuric acid content, since the solubilities of potassium dichromate ($K_2Cr_2O_7$), silver sulfate ($Ag_2SO_4$) and mercury (II) sulfate also change considerably with a change in the sulfuric acid content.

The reagent solution according to the invention contains at least potassium dichromate ($K_2Cr_2O_7$), silver sulfate ($Ag_2SO_4$), water and sulfuric acid, where the sulfuric acid content is between 20 and 50% (w/w).

In a preferred embodiment, the potassium dichromate ($K_2Cr_2O_7$) content in the reagent solution is between 0.1 to 2.5% by weight and the silver sulfate ($Ag_2SO_4$) content is between 0.1 to 2% by weight.

The reagent solution may optionally also contain mercury (II) sulfate.

In a particularly preferred embodiment, the reagent solution consists only of 0.1 to 2.5% by weight of potassium dichromate ($K_2Cr_2O_7$), 0.1 to 2% by weight of silver sulfate ($Ag_2SO_4$), 20 to 50% by weight of sulfuric acid and water.

It has now been found that particularly reproducible results are obtained with reagent solutions according to the invention which contain at least potassium dichromate ($K_2Cr_2O_7$), silver sulfate ($Ag_2SO_4$), sulfuric acid and water and optionally mercury (II) sulfate and have been prepared by mixing at least two individual solutions. An individual solution here contains at least potassium dichromate and water, but no silver sulfate and no mercury (II) sulfate. The other individual solution contains at least silver sulfate and sulfuric acid, but no mercury sulfate and no potassium dichromate. This individual solution particularly preferably contains silver sulfate and concentrated sulfuric acid. If the reagent solution additionally contains mercury sulfate, a third individual solution is prepared which contains at least mercury (II) sulfate, water and sulfuric acid, but no silver sulfate and no potassium dichromate. This third individual solution particularly preferably contains mercury (II) sulfate in 5 to 25% sulfuric acid (v/v).

Preferred compositions of the individual solutions for the preparation of the reagent solution according to the invention are:

between 10 and 20% (w/w) of Hg sulfate in dilute aqueous sulfuric acid (between 10 and 20% (w/w))

between 2.5 and 7.5% (w/w) of silver sulfate in concentrated sulfuric acid (92% (w/w))

between 2.5 and 5% (w/w) of potassium dichromate in water

Particularly preferred compositions are:

15.5% (w/w) Hg sulfate in dilute 14.5% (w/w) sulfuric acid 4.3% (w/w) silver sulfate in 92% (w/w) sulfuric acid 3.6% (w/w) potassium dichromate in water The individual solutions are then mixed for the preparation of the reagent solution according to the invention.

The reagent solution according to the invention is particularly suitable for determination of the COD in samples in which the chloride ions have previously been expelled by treatment with sulfuric acid. The method for the expulsion of chloride ions using sulfuric acid is known to the person skilled in the art. Details can be found in DIN 38409-41, method 41-2. If the method for the expulsion of chloride is carried out in accordance with the provisions of DIN 38409-41, method 41-2, a reduction to a residual chloride content of a maximum of 2 ppm is typically achieved.

The method for the expulsion of chloride using sulfuric acid has to date usually only been used in the case of samples having a chloride content above 1000 mg/l. Samples having a chloride content below 1000 mg/l are usually treated with a reagent solution which contains mercury (II) sulfate. Mercury (II) sulfate masks chloride ions present in the sample. However, mercury (II) sulfate is very toxic and harmful to the environment. The use of mercury (II) sulfate should therefore be avoided as far as possible.

The method according to the invention now offers the possibility of determining the COD of chloride-containing samples photometrically without using mercury (II) sulfate. To this end, the chloride-containing sample—irrespective of whether it has a chloride content above or below 1000 mg/l—is firstly treated with sulfuric acid in order to expel the chloride ions. The photometric determination of the COD is subsequently carried out using the reagent solution according to the invention. Addition of mercury (II) sulfate to the reagent solution is generally unnecessary, since the expulsion using sulfuric acid reduces the chloride content of the sample so much that the chloride remaining in the sample in extremely small amounts does not impair the further measurement.

In order to achieve adequate measurement accuracy, in particular in the case of low COD values, the sample is diluted as little as possible.

In order to expel the chloride, the sample is typically mixed with the sulfuric acid in a sample: sulfuric acid volume ratio between 1:2 and 2:1. If the procedure of the DIN standard is followed, 20 ml of the sample are mixed with 25 ml of concentrated sulfuric acid. The mixture is then typically stirred for 1 to 3 hours, preferably about 2 hours. An absorber cartridge containing absorber material, such as, for example, soda lime, is preferably attached to the reaction vessel. Details can be found in DIN 38409-41, method 41-2.

After the expulsion, not all, but instead only part of the sample amount is typically used for the further determination of the COD. This part is mixed with the reagent solution. The mixing is preferably carried out in a sample: reagent solution volume ratio between 8:1 and 1:5. The mixing is particularly preferably carried out in a volume ratio between 5:1 and 2:1.

The mixture of reagent solution and sample should have a sulfuric acid content between 48 and 65% (w/w).

The mixture is subsequently incubated. The incubation is preferably carried out for 20 to 150 minutes at a temperature between 120 and 180° C.

In order to work in conformity with the standard, the chemical oxidation in the determination, i.e. the incubation, should be carried out between 145° C. and 155° C., ideally at about 150° C., for approximately 2 h.

In order to prevent loss of volatile org. compounds present in the sample, chemical oxidation in a vessel sealed in a gas-tight manner is of major advantage. A cell which can be sealed reversibly is therefore preferably employed in accordance with the invention as reaction vessel.

For the photometric measurement, it is necessary to have a clear unclouded measurement solution. To this end, all components required for the reaction should dissolve in the reaction mixture under the reaction conditions (temperature and pressure). If masking of chloride possibly remaining in the mixture using mercury (II) sulfate is carried out, a precipitate of mercury (II) chloride forms. This settles in the cooling phase typically carried out before the photometric measurement, so that it does not interfere with the photometric measurement.

The photometric measurement is typically carried out by measurement of the absorbance at a wavelength in the range from 300-700 nm. Suitable photometers for this purpose are all those which are suitable for measurements between 300 nm and 700 nm. The formula for calculation of the COD is known to the person skilled in the art and can be found, for example, in DIN ISO 15705.

It has been found that the method according to the invention can be additionally improved and made particularly sensitive if a sulfuric acid whose COD is a maximum of 5 mg/l is used for the expulsion of the chloride and also for the preparation of the reagent solution.

By variation of the mixing ratio between sample and reagent solution and/or measurement at various wavelengths in the range indicated above, the person skilled in the art will be able to adapt the measurement method to samples having a very high or very low COD.

The present invention thus provides for the first time a photometric method for the determination of the COD, with which samples having a high chloride content can also be measured. The method furthermore enabled the determination to be carried out without the toxic and environmentally harmful mercury (II) sulfate.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding applications EP 11009778.9, filed on 12 Dec. 2011, is incorporated into this application by way of reference.

EXAMPLES

Preparation of the Reagent Solutions

The reagent solution is prepared by mixing 0.3 ml of solution A, 1.0 ml of solution B and 0.3 ml of solution C.

Prepare solution A by dissolving 15.5% (w/w) mercury (II) sulfate in 14.5% (w/w) sulfuric acid.

Prepare solution B by dissolving 0.1% (w/w) potassium dichromate in water. Prepare solution C by dissolving 4.3% (w/w) silver sulfate in water.

Equipment

Reaction cell made from Schott Fiolax® clear tubing glass, having an external diameter of 16 mm and an internal diameter of 13.4 mm Filter photometer or spectrophotometer with device for measurement of the reaction cell described at wavelengths in the range from 300-700 nm.

Thermoreactors for incubation of the reaction cell described in the temperature range from 100-180° C.

Magnetic stirrer with adjustable speed from 100-400 rpm

Absorber cartridge for reducing the chloride content in accordance with DIN 38409-41-2

300 ml conical flasks with ground-glass joint for reducing the chloride content in accordance with DIN 38409-41-2

Absorber material for reducing the chloride content in accordance with DIN 38409-41-2 (for example soda lime)

0.3-25.0 ml glass or piston pipettes

Performance of the Method

Add 20 ml of sample to a 300 ml conical flask with ground-glass joint using a glass pipette. Add a magnetic stirrer bar with a length of 30-50 mm. Subsequently add 25 ml of 96% (w/w) sulfuric acid using a glass pipette slowly and with stirring. The temperature of the mixture should be below 40° C. If necessary, the mixture should be cooled in an ice bath.

Fill an absorber cartridge in accordance with DIN 38409-42-2 with a suitable absorber material (for example 5 g of soda lime) and attach to the conical flask with ground-glass joint and seal using a glass stopper (sketch see DIN 38409-42-2).

Place the apparatus described on a magnetic stirrer and stir at a speed of 250 rpm for 2 hours. In the case of samples having a chloride content of above 10 g/l, it is recommended that the absorber material in the absorber cartridge be replaced after 1 hour.

During the reduction of the chloride content, fill the reaction cell with the reaction solution. If a ready-to-use test kit is used, this step is superfluous.

After the reduction of the chloride content, remove 5 ml of the chloride-depleted sample in sulfuric acid using a glass or piston pipette and add to a prepared reaction cell.

Seal the reaction cell, mix and incubate for 2 hours in a pre-heated thermoreactor at 148° C. Remove the hot cell from the thermoreactor and place in a test-tube rack for cooling. After 10 minutes, swirl the cell and replace in the test-tube rack for cooling to room temperature.

Measure the measurement sample in a photometer at 340 nm.

Evaluation

The evaluation is carried out via a calibration function stored in the photometer. The calibration function is determined in accordance with ISO 8466-1 and DIN 38402 A51.

The invention claimed is:

1. Method for the determination of the Chemical Oxygen Demand (COD) content in chloride-containing samples by
   a) expulsion of chloride ions from a sample by treatment with sulfuric acid
   b) mixing of at least some of the sample obtained from step a), with a reagent solution comprising
      0.1 to 2.5% (w/w) potassium dichromate ($K_2Cr_2O_7$)
      0.1 to 2% (w/w) silver sulfate ($Ag_2SO_4$)
      optionally mercury(II) sulfate ($HgSO_4$)
      water
      sulfuric acid
   characterised in that the sulfuric acid content of the reagent solution is between 20 and 50% (w/w) and the reagent solution is prepared by mixing solutions which comprise:
      at least one solution which contains at least potassium dichromate and water, but no silver sulfate and no mercury(II) sulfate, and
      a solution which contains at least silver sulfate and sulfuric acid, but no mercury sulfate and no potassium dichromate
   c) incubation of a mixture from step b) for at least 20 minutes at a temperature above 100° C.
   d) photometric determination of the COD content of the mixture from c).

2. Method according to claim 1, characterised in that method steps b) to d) are carried out in a cell which can be sealed reversibly.

3. Method according to claim 1, characterised in that the expulsion in step a) is carried out using concentrated sulfuric acid.

4. Method according claim 1, characterised in that the incubation in step c) is carried out for 20 to 150 minutes at a temperature between 120 and 180° C.

5. Method according to claim 1, characterised in that the sample and the reagent solution are mixed in step b) in a sample: reagent solution volume ratio between 5:1 and 1:5.

6. Method according to claim 1, characterised in that the reagent solution consists only of 0.1 to 2.5% by weight of potassium dichromate ($K_2Cr_2O_7$), 0.1 to 2% by weight of silver sulfate ($Ag_2SO_4$), 20 to 50% by weight of sulfuric acid and water.

7. Method according to claim 1, characterised in that the photometric determination in step d) is carried out by measurement of the absorbance at a wavelength in the range from 300-700 nm.

8. Method according to claim 1, characterised in that sulfuric acid having a COD of less than 5 mg/l is employed in steps a) and b).

9. Method according to claim 1, characterised in that sulfuric acid having a COD of less than 5 mg/l is used for step a).

* * * * *